US010179147B2

(12) United States Patent
Prestwich et al.

(10) Patent No.: US 10,179,147 B2
(45) Date of Patent: *Jan. 15, 2019

(54) APPLICATIONS OF PARTIALLY AND FULLY SULFATED HYALURONAN

(71) Applicant: University of Utah Research Foundation, Salt Lake City, UT (US)

(72) Inventors: Glenn D. Prestwich, Eastsound, WA (US); Siam Oottamasathein, Salt Lake City, UT (US); Thomas P. Kennedy, Charlotte, NC (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/205,093

(22) Filed: Jul. 8, 2016

(65) Prior Publication Data

US 2016/0361349 A1 Dec. 15, 2016

Related U.S. Application Data

(63) Continuation of application No. 13/702,384, filed as application No. PCT/US2011/039550 on Jun. 8, 2011, now abandoned.

(51) Int. Cl.

| A61K 31/737 | (2006.01) |
|---|---|
| A61K 31/728 | (2006.01) |
| A61K 45/06 | (2006.01) |
| A61K 8/73 | (2006.01) |
| A61Q 11/00 | (2006.01) |
| A61Q 19/08 | (2006.01) |

(52) U.S. Cl.
CPC ............ *A61K 31/737* (2013.01); *A61K 8/735* (2013.01); *A61K 45/06* (2013.01); *A61Q 11/00* (2013.01); *A61Q 19/08* (2013.01)

(58) Field of Classification Search
None
See application file for complete search history.

(56) References Cited

U.S. PATENT DOCUMENTS

| 4,240,163 A | 12/1980 | Galin | |
|---|---|---|---|
| 6,051,701 A * | 4/2000 | Cialdi ................. | A61K 31/737 536/118 |
| 2007/0054878 A1 | 3/2007 | Venbrocks | |

FOREIGN PATENT DOCUMENTS

| DE | 19813234 | | 9/1999 |
|---|---|---|---|
| EP | 0889055 | | 1/1999 |
| JP | H11269077 | | 10/1999 |
| JP | 2001163789 | | 6/2001 |
| KR | 20080026924 | * | 3/2008 |
| WO | 2005046562 | | 5/2005 |
| WO | 2009124266 | | 10/2009 |
| WO | 2010130466 | | 11/2010 |
| WO | 2010130468 | | 11/2010 |
| WO | 2011156445 | | 12/2011 |

OTHER PUBLICATIONS

English translation of KR20080026924 (2008).*
Ogawa et al., "Sulfated hyaluronic acid, a potential selectin inhibitor, ameliorates experimentally induced crescentic glomerulonephritis," Nephron—Experimental Nephrology, 2005, 99:e26-e32 (abstract).
Matsuda et al., "Therapeutic effect of sulphated hyaluronic acid, a potential selectin-blocking agent, on experimental progressive mesangial proliferative glomerulonephritis," J. Pathol., 2002, 190:407-414.
European Search Report for European application No. 1179068.5 dated Jul. 10, 2013.
Hintze et al., "Modifications of hyaluronan influence the interaction with human bone morphogenetic protein-4 (hBMP-4)," Biomacromolecules, 2009, 10:3290:3297.
Nagasawa et al., "Chemical sulfation of preparations of chondroitin 4- and 6-sulfate, and dermatan sulfate. Preparation of chondroitin sulfate like materials from chondroitin 4-sulfate," Carb. Res., 1986, 158:183-190.
Maruyama et al., "Conformational changes and anticoagulant activity of chondroitin sulfate following its O-sulfonation," Carb. Res., 1998, 306:35-43.
Office Action for JP 2013-514324 dated Apr. 24, 2015 (English translation).
Petit et al., "Controlled sulfonation of natural anionic bacterial polysaccharides can yield agents with specific regenerating activity in vivo." Biomacromolecules, 2004, 5:445-452.
International Search Report for PCT/US11/39550 dated Sep. 29, 2011.
Suzuki, "Preparation and inhibitory activity on hyaluronidase of fully O-sulfated hyaluro-oligosaccharides," Glycobiol., 2001, 11:57-64.
Office Action for JP 2015-253460 dated Sep. 21, 2016 (English translation).
Yamamoto et al., "Absorption of water-soluble compounds with different molecular weights and [Asu1.7]-eel calcitonin from various mucosal administration sites," J. Controlled Release, 2001, 76:363-374.
U.S. Office Action for U.S. Appl. No. 15/381,187 dated Apr. 4, 2018, 10pp.
Magnani, A. et al., "Blood-interaction performance of differently sulphated hyaluronic acids," 1996, Thrombosis Research, 81:383-395.
Saary, J. et al., "A systematic review of contact dermatitis treatment and prevention," 2005, J. Am. Acad. Dermatol., 53:845-855 and 845e1-845e13.
English translation of Korean Office Action for KR 10-2013-7027636 dated Mar. 21, 2018, 8pp.
Ogawa, D. et al., "Sulfated hyaluronic acid, a potential selectin inhibitor, ameliorates experimentally induced crescentic glomerulonephritis," 2005, Nephron Exp. Nephrol, 99:e26-e32.

* cited by examiner

*Primary Examiner* — Bong-Sook Baek
(74) *Attorney, Agent, or Firm* — Gardner Groff Greenwald & Villanueva, PC

(57) ABSTRACT

Described herein is the use of partially and fully sulfated hyaluronan or the pharmaceutically acceptable salt or ester thereof for therapeutic and cosmetic applications as well as the treatment of a number of systemic, dermatological, periodontal, ophthalmic, and urological inflammatory diseases.

25 Claims, 5 Drawing Sheets

APPLICATIONS OF PARTIALLY AND FULLY SULFATED HYALURONAN

CROSS REFERENCE TO RELATED APPLICATION

This application is a continuation application of U.S. nonprovisional application Ser. No. 13/702,384, filed Mar. 18, 2013, which is U.S. national phase application under 35 USC § 371 of international application no. PCT/US11/39550 filed on Jun. 8, 2011. These applications are hereby incorporated by reference in their entireties entirety for all of its teachings.

BACKGROUND

Systemic inflammatory diseases such as multiple sclerosis, rheumatoid arthritis, osteoarthritis, diabetic nephropathy, many pulmonary disorders, periodontal disease, and chronic inflammatory skin disorders such as psoriasis, dermatitis, acne, rosacea, photo-dermal ageing are linked to RAGE-mediated signaling and plague people worldwide. To put these diseases into perspective, the National Psoriasis Foundation reports that psoriasis alone afflicts 2-3% of the world's population or approximately 125 million people. These inflammatory conditions can be aesthetically unpleasing and can create serious health issues if left untreated.

Conventionally accepted treatments of these conditions may involve UV phototherapy, corticosteroids and glucocorticoids, acitretin, cyclosporine, and methotrexate. However, each of these treatments may cause serious side effects ranging from immune suppression and liver disease to thinning skin and causing birth defects. Due to partial or complete ineffectiveness, these treatments often leave patients unsatisfied with their results.

In addition to the treatments mentioned above, heparin treatment has also been experimentally explored. Heparin, a sulfated polysaccharide, has traditionally been used almost exclusively as an anti-coagulant, but its anti-inflammatory properties are well known. Heparin and its derivatives have shown some promise in treating these inflammatory diseases. Particularly heparin and its derivatives disrupt at least three important events in inflammatory cascades. First, heparin attaches to and blocks the leukocyte integrins P- and L-selectin. Second, heparin and its derivatives reduce the inflammatory cascade by binding to and inhibiting the cationic PMN protease human leukocyte elastase and cathepsin G, which reduces proteolytic tissue injury by PMNs that escape the first heparin barrier of selectin inhibition. Third, heparin and its derivatives potentially inhibit the interaction of the receptor for advanced glycation end-products (RAGE) with its ligands.

Although heparin and its derivatives have shown promise in treating these inflammatory diseases, treatment with heparin and its derivatives exhibit several major drawbacks. First, heparin and its derivatives are porcine-derived; thus leading to concerns of cross-species transfer of viruses. Second, because of heparin's anticoagulant properties, diabetics, cancer patients, and other patients with poor coagulation status treated with this compound are at risk of excessive bleeding. Third, heparin may induce thrombocytopenia in certain individuals who produce an antibody to the complex of heparin with the cationic protein platelet factor-4 (PF-4), resulting in catastrophic platelet aggregation and generalized paradoxical arterial and venous clotting. Thus, an important unmet need is to formulate compounds which may be used to treat inflammatory diseases while avoiding the myriad of side effects seen in other treatments.

SUMMARY

Described herein is the use of partially and fully sulfated hyaluronan or the pharmaceutically acceptable salt or ester thereof for therapeutic and cosmetic applications as well as the treatment of a number of inflammatory diseases and skin disorders. The advantages of the invention will be set forth in part in the description which follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several aspects described below.

DETAILED DESCRIPTION

Figure 1:
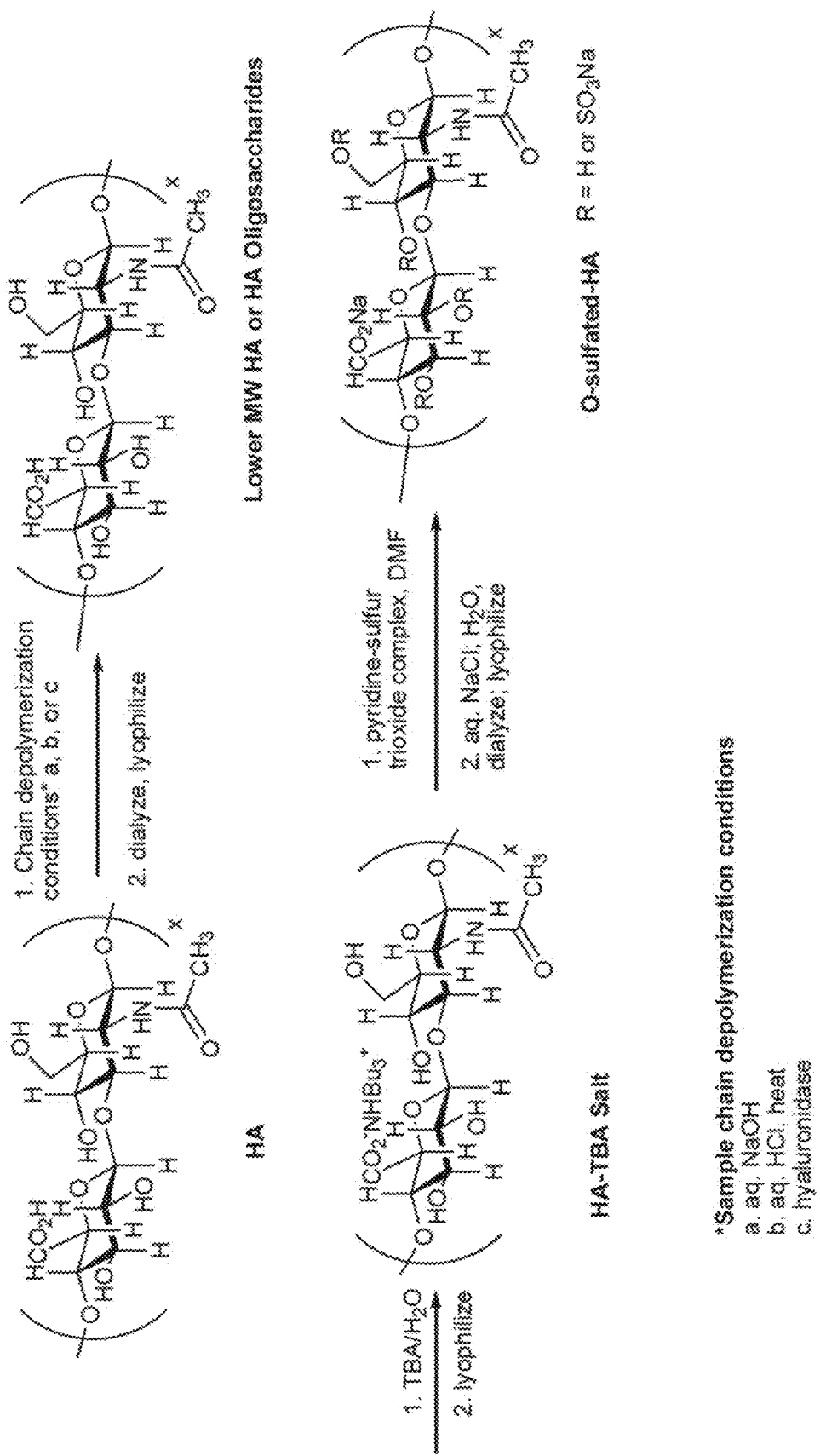
FIG. 1 shows an exemplary synthetic procedure for making partially sulfated hyaluronan by (1) partial depolymerization by controlled hydrolytic chain cleavage, (2) conversion to a tributylammonium salt, and (3) sulfation to produce the partially sulfated hyaluronan.

Before the present compounds, compositions, and/or methods are disclosed and described, it is to be understood that the aspects described below are not limited to specific compounds, synthetic methods, or uses as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

It must be noted that, as used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

"Optional" or "optionally" means that the subsequently described event or circumstance can or cannot occur, and that the description includes instances where the event or circumstance occurs and instances where it does not. For example, the phrase "optionally substituted lower alkyl" means that the lower alkyl group can or can not be substituted and that the description includes both unsubstituted lower alkyl and lower alkyl where there is substitution.

References in the specification and concluding claims to parts by weight, of a particular element or component in a composition or article, denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. For example, hyaluronan that contains at least one —OH group can be represented by the formula Y—OH, where Y is the remainder (i.e., residue) of the hyaluronan molecule.

The term "treat" as used herein is defined as maintaining or reducing the symptoms of a pre-existing condition. The term "prevent" as used herein is defined as eliminating or reducing the likelihood of the occurrence of one or more symptoms of a disease or disorder. The term "inhibit" as used herein is the ability of the compounds described herein to completely eliminate the activity or reduce the activity when compared to the same activity in the absence of the compound.

Described herein is the use of partially and fully sulfated hyaluronan or the pharmaceutically acceptable salt or ester thereof for therapeutic and cosmetic applications as well as the treatment of a number of inflammatory diseases and skin disorders. The term "partially sulfated hyaluronan" as used herein is when the hyaluronan has a degree of sulfation less than 3.5 per disaccharide unit. The term "fully sulfated hyaluronan" as used herein is when the hyaluronan has a degree of sulfation of 3.5 to 4.0 per disaccharide unit. The terms "low molecular hyaluronan" and "hyaluronan oligosaccharide" are defined below. Examples of suitable counterions are provided below.

The hyaluronan starting material can exist as the free acid or the salt thereof. Derivatives of hyaluronan starting material can also be used herein. The derivatives include any modification of the hyaluronan prior to sulfation. A wide variety of molecular weight hyaluronans can be used herein for the depolymerization step. In one aspect, the hyaluronan has a molecular weight greater than 1,000 kDa prior to depolymerization. In another aspect, the hyaluronan can have a molecular weight of 10 kDa to 1,000 kDa prior to depolymerization. A wide variety of hyaluronan molecular weights can also be employed for the sulfation step. In one aspect, the hyaluronan starting material can be converted to low molecular hyaluronan or a hyaluronan oligosaccharide prior to sulfation to produce the partially or fully sulfated hyaluronan. As will be discussed in greater detail below, low molecular weight hyaluronan is hyaluronan that has been degraded with an acid or base. Alternatively, hyaluronan oligosaccharide is produced by degrading hyaluronan with an enzyme such as, for example, hyaluronan synthase or hyaluronidase in a controlled fashion. Subsequently, hyaluronan oligosaccharides having different molecular weights can be separated by GPC or ion exchange separation. FIG. 1 depicts exemplary procedures for producing low molecular hyaluronan or hyaluronan oligosaccharide from hyaluronan.

In one aspect, the low molecular hyaluronan or hyaluronan oligosaccharide being sulfated has a molecular weight from 1 kDa to 2,000 kDa. In another aspect, the low molecular hyaluronan or hyaluronan oligosaccharide being sulfated has a molecular weight from 5 kDa to 500 kDa, 10 kDa to 200 kDa, or 20 kDa to 100 kDa. Exemplary procedures for preparing low molecular weight hyaluronan are provided in the Examples. As discussed above, the molecular weight of the hyaluronan can be modified by cleaving hyaluronan with an acid or base to produce lower molecular weight hyaluronan. In certain aspects, the hyaluronan starting material or a derivative thereof is not derived from an animal source. In these aspects, the hyaluronan can be derived from other sources such as bacteria. For example, a recombinant *B. subtilis* expression system can be used to produce the hyaluronan starting material.

After the low molecular hyaluronan or hyaluronan oligosaccharide has been treated with a base, it is reacted with a sulfating agent to produce the partially or fully sulfated hyaluronan. Sulfating agents commonly used in organic synthesis can be used herein. Examples of sulfating agents include, but are not limited to, pyridine-sulfur trioxide complex or the triethylamine-sulfur trioxide complex. An exemplary synthetic procedure for making partially sulfated hyaluronan is provided in FIG. 1. Referring to FIG. 1, low molecular hyaluronan or hyaluronan oligosaccharide is converted to the tributylamine salt, lyophilized, resuspended in dimethylformamide, and subsequently treated with a sulfating agent (e.g., pyridine-sulfur trioxide complex) to sulfate one or more hydroxyl protons. The fully sulfated hyaluronan can be produced by adding a sufficient amount of base and sulfating agent to sulfate all of the hydroxyl groups.

Figure 4:
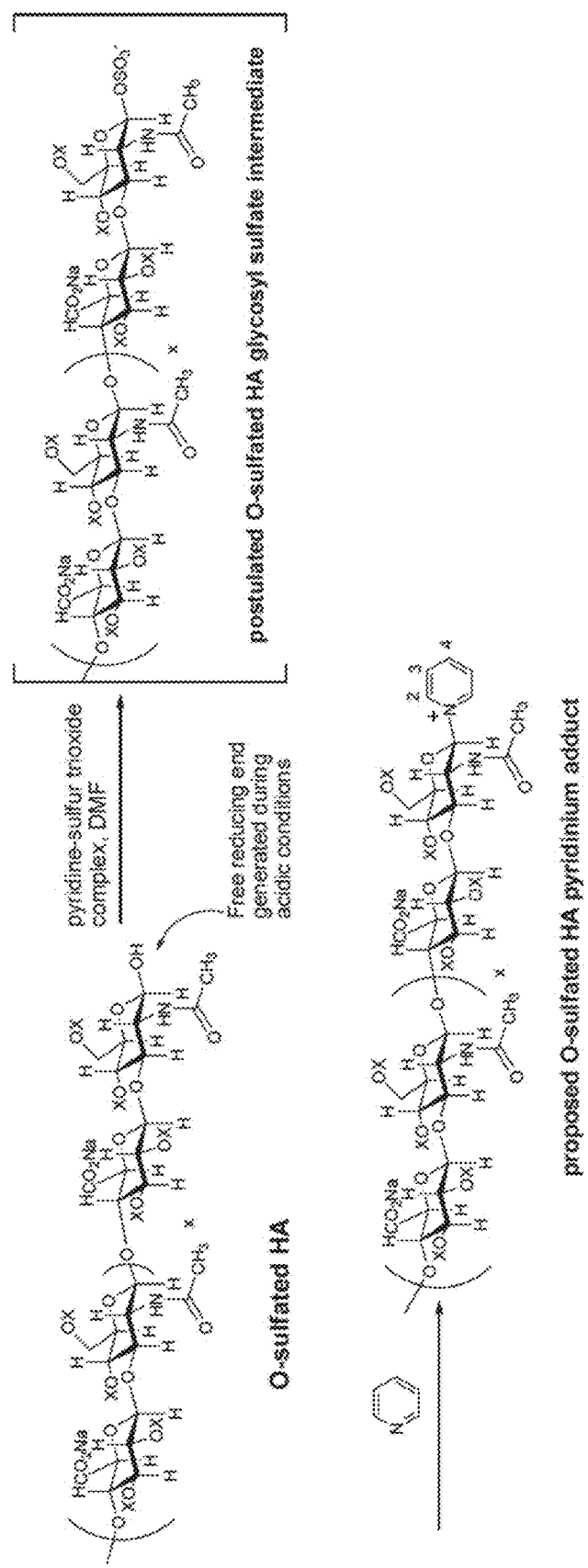
FIG. 4 shows the sulfation and C-pyridinylation of hyaluronan to produce a by-product associated with the production of partially or fully sulfated hyaluronan using the sulfur trioxide-pyridine complex.

In one aspect, when the sulfating agent is a pyridine-sulfur trioxide complex, a pyridinium adduct of the partially or fully sulfated hyaluronan is produced. This is depicted in FIG. 4, where pyridine is covalently attached to the partially or fully sulfated hyaluronan. Not wishing to be bound by theory, when hyaluronan is reacted with the pyridine-sulfur trioxide complex in a solvent such as, for example, DMF, a small amount of acid is produced from traces of water present in situ, which causes partial depolymerization resulting in a free reducing end group (e.g., a hydroxyl group in FIG. 4). The hydroxyl group of the hemiketal can ultimately be sulfated to produce a sulfated intermediate, which subsequently reacts with free pyridine produced in situ to produce the pyridinium adduct. In one aspect, the molecular weight of the pyridinium adduct of the partially or fully sulfated hyaluronan is less than or equal to 10 kDa. In other aspects, the molecular weight is 0.1 kDa, 0.5 kDa, 1 kDa, 2 kDa, 3 kDa, 4 kDa, 5 kDa, 6 kDa, 7 kDa, 8 kDa, 9 kDa, or 10 kDa, where any value can for the lower and upper end-point of a molecular weight range.

In one aspect, the degree of sulfation is from 0.1, 1.0, 1.5, 2.0, 2.5, 3.0, to less than 3.5 or any range thereof per disaccharide unit of the partially sulfated hyaluronan. In one aspect, the average molecular weight of the partially or fully sulfated hyaluronan is less than 100 kDa, less than 50 kDa, less than 25 kDa, less than 10 kDa, or less than 5 kDa. In another aspect, the partially or fully sulfated hyaluronan has an average molecular size from 0.5 kDa to less than 50 kDa, 2 Da to 20 kDa, or 3 kDa to 10 kDa. In a further aspect, the partially or fully sulfated hyaluronan has an average molecular size from 0.5 kDa to 10 kDa or 1 kDa to 5 kDa. Depending upon reaction conditions, one or more different hydroxyl groups present in the low molecular hyaluronan or hyaluronan oligosaccharide can be sulfated. In one aspect, the primary C-6 hydroxyl proton of the N-acetyl-glucosamine residue of the low molecular hyaluronan or hyaluronan oligosaccharide is sulfated. In another aspect, the primary C-6 hydroxyl proton of the N-acetyl-glucosamine residue of hyaluronan and at least one C-2 hydroxyl proton or C-3 hydroxyl proton of a uronic acid residue or at least one C-4 hydroxyl proton of an N-acetyl-glucosamine residue is substituted with a sulfate group. In another aspect, the primary C-6 hydroxyl proton of the N-acetyl-glucosamine residue of the low molecular hyaluronan or hyaluronan oligosaccharide and at least one C-2 hydroxyl proton and C-3 hydroxyl proton of a uronic acid residue and at least one C-4 hydroxyl proton of an N-acetyl-glucosamine residue is substituted with a sulfate group. In another aspect, 0.001%, 0.01%, 0.1%, 1%, 5%, 10%, 20%, 30%, 40%, 50%, 60%, 70%, 80%, 90%, 95%, or less than 100%, or any range thereof of hydroxyl protons present on the low molecular hyaluronan or hyaluronan oligosaccharide can be deprotonated and subsequently sulfated.

The partially or fully sulfated hyaluronan described herein can be the pharmaceutically acceptable salt or ester thereof. In some aspects, the pharmaceutically acceptable ester can be a prodrug. For example, free hydroxyl groups of the partially or fully sulfated hyaluronan can be partially esterified with palmitoyl chloride to afford an amphiphilic compound that is hydrolyzed by endogenous esterases to liberate the free partially or fully sulfated hyaluronan. Other prosthetic groups that liberate non-toxic byproducts familiar to those skilled in the art may also be used. Pharmaceutically acceptable salts are prepared by treating the free acid with an appropriate amount of a pharmaceutically acceptable base. Representative pharmaceutically acceptable bases are ammonium hydroxide, sodium hydroxide, potassium hydroxide, lithium hydroxide, calcium hydroxide, magnesium hydroxide, ferrous hydroxide, zinc hydroxide, copper hydroxide, aluminum hydroxide, ferric hydroxide, isopropylamine, trimethylamine, diethylamine, triethylamine, tripropylamine, benzalkonium, choline, ethanolamine, 2-dimethylaminoethanol, 2-diethylaminoethanol, lysine, arginine, histidine, and the like. In one aspect, the reaction is conducted in water, alone or in combination with an inert, water-miscible organic solvent, at a temperature of from about 0° C. to about 100° C. such as at room temperature.

The molar ratio of partially or fully sulfated hyaluronan to base used is chosen to provide the ratio desired for any particular salt. For preparing, for example, the ammonium salts of the free acid starting material, the starting material can be treated with approximately one equivalent of pharmaceutically acceptable base to yield a neutral salt. In other aspects, choline salts of the partially or fully sulfated hyaluronan can be prepared and used herein.

The partially or fully sulfated hyaluronan described herein can be formulated in any excipient the biological system or entity can tolerate to produce pharmaceutical compositions. Examples of such excipients include, but are not limited to, water, aqueous hyaluronic acid, saline, Ringer's solution, dextrose solution, Hank's solution, and other aqueous physiologically balanced salt solutions. Nonaqueous vehicles, such as fixed oils, vegetable oils such as olive oil and sesame oil, triglycerides, propylene glycol, polyethylene glycol, and injectable organic esters such as ethyl oleate can also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosol, cresols, formalin and benzyl alcohol. In certain aspects, the pH can be modified depending upon the mode of administration. For example, the pH of the composition is from about 5 to about 6, which is suitable for topical applications. Additionally, the pharmaceutical compositions can include carriers, thickeners, diluents, preservatives, surface active agents and the like in addition to the compounds described herein.

The pharmaceutical compositions can also include one or more active ingredients used in combination with the partially or fully sulfated hyaluronan. The resulting pharmaceutical composition can provide a system for sustained, continuous delivery of drugs and other biologically-active agents to tissues adjacent to or distant from the application site. The biologically-active agent is capable of providing a local or systemic biological, physiological or therapeutic effect in the biological system to which it is applied. For example, the agent can act to control and/or prevent infection or inflammation, enhance cell growth and tissue regeneration, control tumor growth, act as an analgesic, promote anti-cell attachment, reduce alveolar bone and tooth loss, inhibit degeneration of cartilage and weight bearing joints, and enhance bone growth, among other functions. Additionally, any of the compounds described herein can contain combinations of two or more pharmaceutically-acceptable compounds. Examples of such compounds include, but are not limited to, antimicrobial agents, antiinflammatory agents, anesthetics, and the like.

The pharmaceutical compositions can be prepared using techniques known in the art. In one aspect, the composition is prepared by admixing the partially or fully sulfated hyaluronan herein with a pharmaceutically-acceptable compound and/or carrier. The term "admixing" is defined as mixing the two components together so that there is no chemical reaction or physical interaction. The term "admixing" also includes the chemical reaction or physical interaction between the compound and the pharmaceutically-acceptable compound. Covalent bonding to reactive therapeutic drugs, e.g., those having nucleophilic groups, can be undertaken on the compound. Second, non-covalent entrapment of a pharmacologically active agent in a cross-linked polysaccharide is also possible. Third, electrostatic or hydrophobic interactions can facilitate retention of a pharmaceutically-acceptable compound in the compounds described herein.

It will be appreciated that the actual preferred amounts of the partially or fully sulfated hyaluronan in a specified case will vary according to the specific compound being utilized, the particular compositions formulated, the mode of application, and the particular situs and subject being treated. Dosages for a given host can be determined using conventional considerations, e.g. by customary comparison of the differential activities of the subject compounds and of a known agent, e.g., by means of an appropriate conventional pharmacological protocol. Physicians and formulators, skilled in the art of determining doses of pharmaceutical compounds, will have no problems determining dose according to standard recommendations (Physicians Desk Reference, Barnhart Publishing (1999).

The pharmaceutical compositions described herein can be administered in a number of ways depending on whether local or systemic treatment is desired, and on the area to be treated. Administration can be topically (including ophthalmically, vaginally, rectally, intranasally, orally, or directly to the skin). Administration for periodontal disease or gingivitis can be topically via delivery of a gel, paste, or rinse to the diseased gums or periodontal pockets. The active ingredient can also be formulated as a coating on floss, periodontal brushes, periodontal probes or other oral health care devices. Formulations for topical administration can include ointments, lotions, creams, gels, drops, suppositories, sprays, liquids and powders. Conventional pharmaceutical carriers, aqueous, powder or oily bases, thickeners and the like can be necessary or desirable. Administration can also be directly into the lung by inhalation of an aerosol or dry micronized powder. Administration can also be by direct injection into the inflamed or degenerating joint space.

Preparations for administration include sterile aqueous or non-aqueous solutions, suspensions, and emulsions. Examples of non-aqueous carriers include water, alcoholic/aqueous solutions, emulsions or suspensions, including saline and buffered media. Parenteral vehicles, if needed for collateral use of the disclosed compositions and methods, include sodium chloride solution, Ringer's dextrose, dextrose and sodium chloride, lactated Ringer's, or fixed oils. Intravenous vehicles, if needed for collateral use of the disclosed compositions and methods, include fluid and nutrient replenishers, electrolyte replenishers (such as those based on Ringer's dextrose), and the like. Preservatives and other additives can also be present such as, for example, antimicrobials, anti-oxidants, chelating agents, and inert gases and the like.

Dosing is dependent on severity and responsiveness of the condition to be treated, but will normally be one or more doses per day, with course of treatment lasting from several days to several months or until one of ordinary skill in the art determines the delivery should cease. Persons of ordinary skill can easily determine optimum dosages, dosing methodologies and repetition rates.

The partially or fully sulfated hyaluronan can be used in a variety of applications related to the treatment of inflammatory skin disorders, treatment of inflammatory dental disorders, treatment of inflammatory respiratory disorders, treatment of inflammatory eye disorders, burn injury healing, and tissue regeneration/engineering. In one aspect, the partially or fully sulfated hyaluronan and compositions described herein can improve wound healing in a subject in need of such improvement. The partially or fully sulfated hyaluronan and pharmaceutical compositions described herein can be placed directly in or on any biological system without purification as it is composed of biocompatible materials. Examples of sites the partially sulfated hyaluronan can be placed include, but are not limited to, soft tissue such as muscle or fat; hard tissue such as bone or cartilage; areas of tissue regeneration; a void space such as periodontal pocket; surgical incision or other formed pocket or cavity; a natural cavity such as the oral, vaginal, rectal or nasal cavities, the joint space, the cul-de-sac of the eye, and the like; the peritoneal cavity and organs contained within, and other sites into or onto which the compounds can be placed including a skin surface defect such as a cut, scrape or burn area. It is contemplated that the tissue can be damaged due to injury or a degenerative condition or, in the alternative, the partially or fully sulfated hyaluronan and compositions described herein can be applied to undamaged tissue to prevent injury to the tissue. The partially or fully sulfated hyaluronan can be biodegradable and naturally occurring enzymes will act to degrade them over time. Components of the partially or fully sulfated hyaluronan can be "bioabsorbable" in that the components of the partially sulfated hyaluronan will be broken down and absorbed within the biological system, for example, by a cell, tissue and the like. Additionally, partially or fully sulfated hyaluronan, especially those that have not been rehydrated, can be applied to a biological system to absorb fluid from an area of interest.

In the case of inflammatory skin disorders such as psoriasis, acne, atopic dermatitis, rosacea or UV light dependent photo-aging (i.e., photo-dermal ageing), the partially or fully sulfated hyaluronan can be applied topically as part of an emollient to prevent or treat the intended condition. In the case of respiratory disorders such as asthma, chronic obstructive pulmonary disease, acute lung injury or cystic fibrosis, the partially sulfated hyaluronan can be dissolved in a water-soluble isotonic vehicle compatible with airway lining fluid and delivered to the lung or nasal passages as an inhaled aerosol. Alternatively, the partially or fully sulfated hyaluronan can be formulated into a micronized powder and inhaled into the lung as a dry powder. In the case of eye diseases, the partially or fully sulfated hyaluronan can be placed into an aqueous vehicle and applied to the eye topically as drops, or injected directly into the eye either by needle or using an implanted constant drug delivery device. In the case of dental disorders such as periodontal disease, the partially or fully sulfated hyaluronan can be added as a component of a mouthwash or formulated into creams or gingival packing materials to be applied directly to the gingival crevice.

The partially or fully sulfated hyaluronan can also be injected parenterally either intravenously, intramuscularly or subcutaneously to treat or prevent systemic inflammatory disorders such as diabetic vascular or renal disease or inflammatory gastrointestinal diseases. Similarly, the partially sulfated hyaluronan can be injected intra-articularly to treat inflammatory and degenerative arthritis. The partially or fully sulfated hyaluronan can also be administered orally in capsules or formulated into an enema to be delivered intra-rectally as treatment for inflammatory bowel diseases.

The partially or fully sulfated hyaluronan and compositions described herein can deliver at least one pharmaceutically-acceptable compound to a patient in need of such delivery, comprising contacting at least one tissue capable of receiving the pharmaceutically-acceptable compound with one or more compositions described herein. The partially or fully sulfated hyaluronan can be used as a carrier for a wide variety of releasable biologically active substances having curative or therapeutic value for human or non-human animals. Many of these substances that can be carried by the partially or fully sulfated hyaluronan are discussed above. Included among biologically active materials which are suitable for incorporation into the gels of the invention are therapeutic drugs, e.g., anti-inflammatory agents, antipyretic agents, steroidal and non-steroidal drugs for anti-inflammatory use, hormones, growth factors, contraceptive agents, antivirals, antibacterials, antifungals, analgesics, hypnotics, sedatives, tranquilizers, anti-convulsants, muscle relaxants, local anesthetics, antispasmodics, antiulcer drugs, peptidic agonists, sympathiomimetic agents, cardiovascular agents, antitumor agents, oligonucleotides and their analogues and so forth. A biologically active substance is added in pharmaceutically active amounts.

In one aspect, the partially or fully sulfated hyaluronan described herein can inhibit the activity of the receptor for Advanced Glycation Endproducts (RAGE), P-selectin, L-selectin, human leukocyte elastase, or any combination thereof. In another aspect, the partially or fully sulfated hyaluronan can reduce or inhibit the activity of a cationic polypeptide. RAGE is highly expressed in human skin, where it is present on dermal fibroblasts, dendritic cells, keratinocytes, endothelial cells and monocytes. RAGE is upregulated in sun-exposed skin by Advanced Glycation End-Products (AGE) and by the cytokine tumor necrosis factor-α. RAGE plays a prominent role in UV-induced photo-ageing (i.e., photo-dermal ageing), where its ligation by AGE products such as UV-induced carboxymethyl lysine (CML) promotes skin aging through stimulation of extracellular matrix production by dermal fibroblasts. The role of RAGE is likely to be even more prominent in psoriasis because this disease is critically dependent on activated T-lymphocytes for initiation of inflammation. T-lymphocytes may also be mechanistically important in acne and atopic dermatitis. In the case of acne, elevated dermal levels of $CD3^+$ and $CD4^+$ T lymphocytes and macrophages stimulate hyper-proliferation of keratinocytes in the ducts of follicles, producing the plugged follicular ducts that lead to formation of the acne comedone. In the case of atopic dermatitis, dermal antigens activate $T_H2$ lymphocytes which secrete cytokines such as interleukin-4 (IL-4) and interleukin-13 (IL-13), resulting in the recruitment of eosinophils into skin. Eosinophils, in turn, release cationic toxins such as major basic protein, which produces allergic skin disease. Thus, the potent RAGE inhibiting activity of the compounds described herein makes them useful in treating a variety of skin disorders including, but not limited to, acne, eczema, atopic dermatitis, psoriasis, or photo-dermal ageing.

RAGE is a cell surface receptor, expressed on a range of cells, including endothelium, fibroblasts and mononuclear phagocytes. In diabetic patients, hyperglycemia leads to non-enzymatic glycation and oxidation of proteins and lipids to form advanced glycation end products (AGEs). In smokers, AGE products accumulate in the front of the mouth, the lungs, and systemically. Smokers are also highly susceptible to focal gum diseases, periodontitis, and tooth loss from inflammatory disease. AGEs are ligands for the RAGE receptor, and ligation leads to an inflammatory cascade. In murine diabetic models, it has been shown this ligation provides a central role in oral infection, exaggerated inflammatory response, and destruction of alveolar bone leading to tooth loss. Expression of RAGE in gingival tissues has been demonstrated in patients with chronic periodontitis with and without type 2 diabetes. Efforts to block periodontal RAGE may be best performed via local delivery.

The partially or fully sulfated hyaluronan described herein are antagonists to RAGE-mediated inflammation. As RAGE ligation is a fundamentally prominent mechanism of perpetuating inflammatory signaling, inhibiting ligation and thus suppressing up-regulation of RAGE is an effective treatment to reduce this form of inflammatory cell perturbation. The compounds described herein block the RAGE receptor, keeping ligands from binding and activating the RAGE inflammatory mechanism. Low molecular weight and water soluble sulfated hyaluronan lack anti-coagulant activity, and are thus generally considered safe for systemic and topical uses. In gingivitis, periodontitis, and post-implantation of dental implants, a locally administered partially or fully sulfated hyaluronan could lead to the preservation of gingival tissue and bone.

In the adult state, RAGE is not always so entirely helpful to the organism. Malignant tumors secrete amphoterin (or high mobility box group protein-1, HMGB-1) as an autocrine factor and use the interaction of amphoterin with RAGE to promote primary tumor growth and metastasis. Blocking RAGE with a recombinant decoy (soluble RAGE or s-RAGE) reduces tumor growth and inhibits metastasis. During sepsis, monocytes and macrophages secrete amphoterin which interacts with RAGE on blood vessels and other inflammatory cells to enhance the severity of bacterial shock. Blocking this interaction with antibodies against RAGE prevents organ damage in severe sepsis. In the adult state, RAGE also functions as a vascular adhesion receptor promoting the recruitment of PMNs, monocytes and lymphocytes into areas of inflammation. Blocking RAGE blunts inflammatory cell influx. This has been previously demonstrated in animal models of multiple sclerosis, where competitive blockade of vascular endothelial RAGE with s-RAGE prevents the influx of activated encephalitogenic T-lymphocytes into the central nervous system, and retards onset and progression of neurologic inflammation and degeneration.

RAGE also interacts with a family of calcium binding proteins called S100 calgranulins, which are secreted by PMNs, monocytes and lymphocytes as potent inflammation-promoting factors. Elevated levels of S100 calgranulins are a prominent marker of PMN inflammation in acute lung injury and in the airway secretions of patients with cystic fibrosis. In the eye, the interaction of S100 calgranulins with RAGE plays a prominent role leading to blindness in age-related macular degeneration. RAGE also binds the Alzheimer's β-amyloid peptide and the β sheets of amyloid proteins. Through RAGE-related induction of neural cell death and inflammation, RAGE-β sheet fibrillar interactions mediate Alzheimer's dementia and organ damage in systemic amyloidosis.

RAGE is also prominent in diabetes mellitus. When blood glucose is elevated, the aldehyde group of glucose randomly attaches to the amines of cellular proteins, creating covalent adducts. In the presence of oxidants such as hypochlorous acid (HOCl), the oxidant produced by PMNs, this glucose moiety can then become oxidized. These oxidized, glycosylated proteins are known as Advanced Glycation End-Products, (AGE). AGEs also bind the RAGE receptor avidly, and trigger RAGE-mediated signaling. AGE-RAGE signaling accounts for the vascular endothelial dysfunction, poor wound healing and accelerated arterial atherosclerosis characteristic of poorly controlled diabetes. In the eye, AGE-RAGE signaling produces the proliferation of retinal microvessels that leads to diabetic retinopathy and blindness. In the kidney, AGE-RAGE signaling accounts for the initial renal hypertrophy and then fibrosis that causes diabetic renal failure (diabetic nephropathy). AGE-RAGE signaling likewise produces apoptosis of endothelium, inhibits blood vessel growth and retards healing of cutaneous diabetic ulcers.

The ability of the partially or fully sulfated hyaluronan to block RAGE makes it particularly valuable as therapeutic agents for inflammation. RAGE functions in utero as a receptor binding the growth promoting nuclear protein amphoterin, or high mobility box protein-1 (HMGB-1). There, the amphoterin-RAGE interaction triggers growth signaling important for nervous system development. In the adult state, RAGE is expressed in the cells of vessel walls, neural tissues, cardiac myocytes, monocytes and macrophages, T-lymphocytes, renal mesangial cells, and in skin fibroblasts, dendrocytes and keratinocytes. Thus, in one aspect, the partially or fully sulfated hyaluronan and compositions described herein can be used to safely reduce or prevent inflammation in a subject produced by a variety of different maladies attributed to RAGE-related diseases including, but not limited to, cancer, multiple sclerosis, osteoarthritis, cystic fibrosis, sickle cell anemia, a cardiovascular inflammatory disorder, or a cardiovascular inflammatory disorder, or diabetic complications.

In other aspects, the partially or fully sulfated hyaluronan and compositions, as negatively charged entities, can also be administered to bind and inhibit cationic skin peptides derived from cathelicidins, thereby treating or preventing skin disorders. For example, the skin condition known as acne rosacea, which is known to occur from excess skin expression of active cathelicidin peptides, can be treated or prevented using the partially or fully sulfated hyaluronan described herein. Examples of skin disorders that can be treated or prevented using the partially or fully sulfated hyaluronan include, but are not limited to, rosacea, atopic dermatitis (eczema), allergic contact dermatitis, psoriasis, dermatitis herpetiformis, acne, diabetic skin ulcers and other diabetic wounds, burns (including relieving pain of thermal burns), sunburn (including relieving pain of sunburn), prevention of scarring after plastic surgery, actinic keratoses, inflammation from insect bites, poison ivy, radiation-induced dermatitis/burn, facilitation of skin healing, prevention and treatment of keloid scarring, photo-dermal ageing, or the treatment of seborrheic dermatitis.

Due to the ability of the partially or fully sulfated hyaluronan to inhibit RAGE activity and other biological mechanisms, the partially or fully sulfated hyaluronan has numerous therapeutic applications in addition to treating or preventing skin disorders. In one aspect, the partially or fully sulfated hyaluronan can be used in dental and oral surgery to treat gingivitis (periodontal disease) and aphthous ulcers.

In other aspects, the partially or fully sulfated hyaluronan can be used in ophthalmological applications such as, for example, in the treatment of age-related macular degeneration, diabetic retinopathy, dry eye syndrome and other inflammatory conjunctivitis, iritis, uveitis, allergic conjunctivitis, anti-inflammatory aid in cataract surgery, or in the prevention of corneal inflammation and scarring. In one aspect, the partially or fully sulfated hyaluronan can be administered intraocularly or directly to the surface of the eye.

In further aspects, the partially or fully sulfated hyaluronan can be used in genitourinary applications (e.g., prevention of urinary tract infection, treatment of the transitional cell cancer of the bladder and uroepithelial system; treatment of interstitial cystitis; and use as a vaginal lubricant/protective to prevent transmission of sexually transmitted diseases).

In another aspect, the partially or fully sulfated hyaluronan can be used to treat a number of respiratory disorders including cystic fibrosis, bronchiectasis, rhinitis (both allergic and perennial), sinusitis, emphysema and chronic bronchitis (COPD), acute lung injury/adult respiratory distress syndrome, interstitial lung fibrosis, SARS, asthma, and respiratory syncytial virus. In other aspects, the partially or fully sulfated hyaluronan can prevent and treat snoring and obstructive sleep apnea, prevent infection by common respiratory pathogens (*Stretococcus pneumoniae, Hemophilus influenzae, Staphylococcus, Mycoplasma pneumoniae*, Chlamydial pneumonia, Gram negative enteric infections) in immune suppressed hosts such as subjects who are HIV positive or who have hematopoietic malignancies, or prevent and treat otitis media.

The partially or fully sulfated hyaluronan can be used in cardiovascular applications (e.g., treating or preventing acute coronary syndrome or atherosclerosis); hematological/oncological applications (e.g., prevention and treatment of sickle cell anemia; prevention and treatment of metastatic disease; and prevention of hypercoagulable state of malignancy (Trousseau's syndrome)); treatment of infectious diseases (e.g., cerebral vascular occlusive syndromes and nephritis in Falciparum malaria, Yellow fever, Denge fever, systemic sepsis, and adjunctive treatment of HIV to prevent viral fusion with and infection of target cells); treatment of gastrointestinal diseases (e.g., ulcerative colitis, Crohn's disease of the bowel, Hemorrhoids, and the prevention of stress ulceration of the stomach and esophagus); treatment of rheumatological and immunological diseases (e.g., prevention and treatment of osteoarthritis, rheumatoid arthritis, systemic lupus erythematosis, prevention and treatment of angioneurotic edema, Sjogren's syndrome, systemic sclerosis, systemic amyloidosis, and systemic mastocytosis); renal diseases (e.g., prevention and treatment of diabetic nephropathy and glomerulonephritis); and neurologic diseases (e.g., multiple sclerosis and Alzheimer's dementia).

In one aspect, the partially or fully sulfated hyaluronan can be used to treat or prevent urological inflammation. The term "urological inflammation" as used herein is defined as inflammation associated with any part or region of the genitourinary system. Urological inflammation includes, but is not limited to, inflammation of the bladder, urethra, urothelium lining, kidney, prostate, vagina, uterus, or any combination thereof. In this aspect, the partially or fully sulfated hyaluronan can be injected parenterally, either intravenously, intramuscularly or subcutaneously, to treat or prevent systemic urological inflammatory disorders. Similarly, the modified hyaluronan or partially/fully sulfated hyaluronan can also be administered orally in capsules, in tablets, in chewing gum, in lozenges, in powders, or in a beverage. Alternatively, the modified hyaluronan or partially/fully sulfated hyaluronan can be administered by intravesical installation (i.e., via a catheter).

In one aspect, the partially and fully sulfated hyaluronan described herein can inhibit the activity of LL-37 in a subject. LL-37 is a host defense peptide produced from the C-terminus of the hCAP18 precursor protein and is produced in circulating neutrophils, cells of the mucosal epithelium, keratinocytes, myeloid bone marrow cells, epithelial cells of the skin, gastrointestinal tract, epididymis gland and lungs. LL-37 is produced by epithelial cells (urothelial cells) of the urinary tract in both humans and mice, with significantly elevated urinary levels during episodes of kidney and/or bladder infections (pyelonephritis or cystitis). In addition to the role that LL-37 has in eradicating microbes, it is immunomodulatory and triggers inflammation via the promotion of leukocyte chemotaxis, angiogenesis, stimulating mast cell degranulation, enhancing neutrophil function, inducing chemokines including IL-8, regulating inflammatory responses via NF-κB, and increasing expression of extracellular matrix components. While the details of the downstream inflammatory mechanisms of action for LL-37 are not completely understood, responses involve the activation of a number of cell-surface receptors and signaling pathways.

Based on the link between elevated levels of LL-37 and the occurrence of urological inflammation, described herein is a method for screening a compound's ability to treat or prevent urological inflammation in a subject. In one aspect, the method involves:

administering to a laboratory animal an amount of LL-37 that induces inflammation in the subject;

administering to the animal prior to step (a) and/or after step (a) the compound; and comparing the amount of inflammation in the animal to a control animal that was administered the same amount of LL-37 but not the compound.

In one aspect, a murine model can be used to screen the ability of different compounds to inhibit LL-37 and, thus, treat or prevent urological inflammation. Exemplary procedures for screening compounds useful in the treatment and prevention of urological inflammation are provided in the Examples.

The partially or fully sulfated hyaluronan and compositions described herein are safer than other related therapies. For example, heparin and other sulfated polysaccharides can reduce diabetic complications in both animal and clinical studies, and are particularly effective against diabetic nephropathy. However, heparins cannot be used in general clinical settings to prevent diabetic complications because the anticoagulant properties present an excessive risk of bleeding. The partially or fully sulfated hyaluronan and compositions described herein possess low anticoagulant activity, which is an important consideration for long-term treatment, which is demonstrated below in the Examples. Additionally, the partially or fully sulfated hyaluronan and compositions have little to no toxicity, which is also demonstrated in the Examples.

EXAMPLES

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

I. Preparation of Sulfated Low Molecular Weight Hyaluronan (LMW-HA) from Base-Treated Hyaluronan a. Base-Treated LMW HA HA (2 g, 67 kDa) was dissolved in 20 mL of NaOH (40% w/v) in a 100 mL beaker and the mixture was stirred for 2 h at room temperature to partially depolymerize the HA by inducing strand cleavage. The resulting viscous liquid was transferred to a 400 mL beaker that contained 100 mL of isopropanol and stirred for 24 h at room temperature. The resulting solution was gravity filtered (filter paper) and the crude product was collected, dissolved in 250 mL of distilled water, and the pH was adjusted to 7.0. The solution was dialyzed against distilled water for 24 h, changing the water bath 4 times during this period, and then lyophilized to dryness to obtain 1.2 g of the base-treated HA. The size of this product can be determined by HPLC<GPC or electrophoresis, and is generally in the range of 5 kDa to 20 kDa.

b. LMW Partially O-Sulfated Base-Treated HA

To obtain the tributylamine (TBA) salt of LMW HA, 0.2 mL of TBA was added to base-treated HA (0.2 g) in 20 mL of distilled water. The mixture was stirred vigorously and lyophilized to dryness. The resulting salt (LMW HA-TBA) was dissolved in 20 mL of N,N-dimethylformamide (DMF) to which the required excess (6 mol/equivalent of total hydroxyl groups in HA, 4 per disaccharide) of pyridine-sulfur trioxide complex (0.325 g) was added. After 3 hours at 40° C., the reaction was quenched by addition of 20 mL of water, and the crude material was precipitated by adding 30 mL of cold ethanol saturated with anhydrous sodium acetate. The crude sulfated product was collected by filtration, dissolved in distilled water (30 mL) and dialyzed against 100 mM NaCl solution (changing solution six times) and against water (change water two times) for two days, changing the solution four times a day, and lyophilized to dryness. The yield of the product was 61% (0.22 g). Based on $^1$H NMR, the degree of substitution was approximately 0.5-1. Elemental analysis gave a sulfur content of 4.13%. The average molecular weight was determined by GPC to be 6,100, and the polydispersity was 2.3.

c. LMW Fully O-Sulfated Base-Treated HA

To obtain the tributylamine (TBA) salt of HA, 0.2 mL of TBA was added to base-treated HA (0.2 g) in 20 mL of distilled water. The mixture was stirred vigorously and lyophilized to dryness. The resulting salt (LMW HA-TBA) was dissolved in 20 mL of N,N-dimethylformamide (DMF) to which the required excess (16 mol/equivalent of available hydroxy group in HA) of pyridine-sulfur trioxide complex (11.0 g) was added. After 3 h at 40° C., the reaction was quenched by the addition of 20 mL of water and the crude product was precipitated by adding 30 mL of cold ethanol saturated with anhydrous sodium acetate. The sulfated product was collected by filtration, dissolved in distilled water (30 mL), and dialyzed against 100 mM NaCl solution (changing solution six times) and against water (change water two times) for two days, changing the solution four times a day, and lyophilized to dryness to give 0.26 g of product (60% yield). The product was characterized by $^1$H NMR and showed an approximate substitution degree of about 3.5. Elemental analysis gave a sulfur content of 13.22%. The average molecular weight was determined by GPC to be 5,900, with a polydispersity of 2.2.

II. Preparation of Sulfated Low Molecular Weight Hyaluronan (LMW-HA) from Acid-Treated Hyaluronan a. Fully O-Sulfated Low MW HA (F-OSHA(1)-10,000)

To obtain the tributylamine (TBA) salt of HA, 0.2 mL of TBA was added to HA (0.2 g, ca. 10,000 Da, degraded from 1.3 MDa HA) in 20 mL of distilled water. The mixture was mixed vigorously and lyophilized to dryness. The resulting salt (HA-TBA) was dissolved in 20 mL of N,N-dimethylformamide (DMF) to which the required excess (6 mol/ equivalent of available hydroxyl groups in HA) of pyridine-sulfur trioxide complex (0.325 g) was added. After 3 h at 40° C., the reaction was quenched by the addition of 20 mL of water and the crude material was precipitated by adding 30 mL of cold ethanol saturated with anhydrous sodium acetate. The sulfated product was collected by filtration, dissolved in distilled water (30 mL), and dialyzed against 100 mM NaCl solution (changing solution six times) and against water (change water two times) for two days, changing the solution four times a day, and lyophilized to dryness to give 0.19 g of product (58% yield). Elemental analysis gave a sulfur content of 12.62%, indicating sulfation of 3.0-3.5. The molecular weight was less than 3,000 Da, suggesting acidic depolymerization during sulfation and workup.

b. Fully O-Sulfated Low MW HA (F-OSHA(2)-10,000)

To obtain the tributylamine (TBA) salt of HA, 0.2 mL of TBA was added to acid-modified 10,000 MW HA (0.2 g) in 20 mL of distilled water. The mixture was mixed vigorously and lyophilized to dryness. The resulting salt (HA-TBA) was dissolved in 20 mL of DMF to which the required excess (16 mol/equivalent of available hydroxyl group in HA) of pyridine-sulfur trioxide complex (1.1 g) was added. After 3 hours at 40° C., the reaction was quenched by addition of 20 mL of water and the crude material was precipitated by adding 30 mL of cold ethanol saturated with anhydrous sodium acetate. The sulfated product was collected by filtration, dissolved in distilled water (30 mL), and dialyzed against 100 mM NaCl solution (changing solution six times) and against water (change water two times) for two days, changing the solution four times a day, and lyophilized to give 0.23 g of product (62% yield). The product was characterized by $^1$H NMR and showed a substitution degree of 3.0-3.5. Elemental analysis gave a sulfur content of 12.10%. The molecular weight was less than 3,000 Da.

c. Fully O-Sulfated Low MW HA (Kewpie Hyalo-Oligo—Pyr.SO$_3$)

Kewpie Hyalo-Oligo HA (200 mg, 0.5 mmole, 8.4 kDa) was dissolved in 10 mL of DMF. TBA (1 eq. 0.5 mmole, 0.12 mL) was added while stirring and stirred for an additional 10 minutes. The required excess (6 mol/equivalent of available hydroxyl groups in HA) of pyridine-sulfur trioxide complex (24 eq. 12 mmole, 1.916 g) was added. After stirring for 3 hours at 40° C., the reaction was quenched by the addition of 15 mL of water, and the crude material was precipitated by adding 25 mL of cold ethanol saturated with anhydrous sodium acetate. The sulfated product was collected by filtration, dissolved in 25 mL of distilled water and dialyzed against 100 mM NaCl solution (changing solution six times) and against water (changing water two times) for two days, changing the solution four times a day, and lyophilized to dryness to give 0.175 g of product (51% yield). The product was characterized by $^1$H NMR and showed a substitution degree of greater than 3.5. The average molecular weight was determined by GPC to be 6,800 Da with a polydispersity of 1.88.

d. Fully O-Sulfated Low MW HA (Novozymes-Pyr.SO$_3$)

Novozymes HA (200 mg, 0.5 mmole) degraded to 11 kDa was dissolved in 10 mL of DMF. TBA (1 eq. 0.5 mmole, 0.12 mL) was added while stirring, and the mixture was stirred for an additional 10 minutes. The required excess (6 mol/equivalent of available hydroxyl groups in HA) of pyridine-sulfur trioxide complex (24 eq. 12 mmole, 1.916 g) was next added. After stirring for 3 hours at 40° C., the reaction was quenched by the addition of 15 mL of water, and the crude material was precipitated by adding 25 mL of cold ethanol saturated with anhydrous sodium acetate. The sulfated product was collected by filtration, dissolved in 25 mL of distilled water and dialyzed against 100 mM NaCl solution (changing solution six times) and against water (changing water two times) for two days, changing the solution four times a day, and lyophilized to dryness to give 0.194 g of product (57% yield). The product was characterized by $^1$H NMR and showed a substitution degree of about 3.0-3.5. The average molecular weight was determined by GPC to be 8,100 Da with a polydispersity of 2.00.

e. Partially O-Sulfated Low MW HA (Novozymes-Pyr.SO$_3$)

Novozymes HA (400 mg, 1.0 mmole) degraded to 11 kDa was dissolved in 25 mL of DMF. TBA (1 eq. 1.0 mmole, 0.24 mL) was added while stirring, and stirred for an additional 10 minutes. The required excess (3 mol/equivalent of available hydroxyl groups in HA) of pyridine-sulfur trioxide complex (12 eq. 12 mmole, 1.908 g) was added. After stirring for 3 hours at 40° C., the reaction was quenched by the addition of 30 mL of water, and the crude material was precipitated by adding 50 mL of cold ethanol saturated with anhydrous sodium acetate, and then collected by filtration. The resulting crude partially O-sulfated HA was dissolved in 40 mL of distilled water and dialyzed against 100 mM of NaCl solution (changing solution six times) and against water (changing water two times) for two days, changing the solution four times a day, and lyophilized to dryness to give 0.386 g of product (56% yield). The product was characterized by $^1$H NMR and showed a substitution degree of 2.0. The average molecular weight was determined by GPC to be 9,500 Da with a polydispersity of 1.77.

e. Fully O-Sulfated Low MW HA (Novozymes-DMF.SO$_3$)

Novozymes HA (200 mg, 0.5 mmole) degraded to 11 kDa was dissolved in 10 mL of DMF. TBA (1 eq. 0.5 mmole, 0.12 mL) was added while stirring, and the mixture was stirred for an additional 10 minutes. The required excess (6 mol/equivalent of available hydroxyl groups in HA) of DMF-sulfur trioxide complex (24 eq. 12 mmole, 1.836 g) was added. After stirring for 3 hours at 30° C., the reaction was quenched by the addition of 15 mL of water, and the crude material was precipitated by adding 25 mL of cold ethanol saturated with anhydrous sodium acetate, and then collected by filtration. The resulting crude fully O-sulfated HA was dissolved in 25 mL of distilled water and dialyzed against 100 mM of NaCl solution (changing solution six times) and against water (changing water two times) for two days, changing the solution four times a day, and lyophilized to dryness to give 0.057 g of product (17% yield). The product was characterized by $^1$H NMR and showed a substitution degree of about 3.0-3.5. The average molecular weight was determined by GPC to be 1,900 Da with a polydispersity of 2.48.

Figure 3:
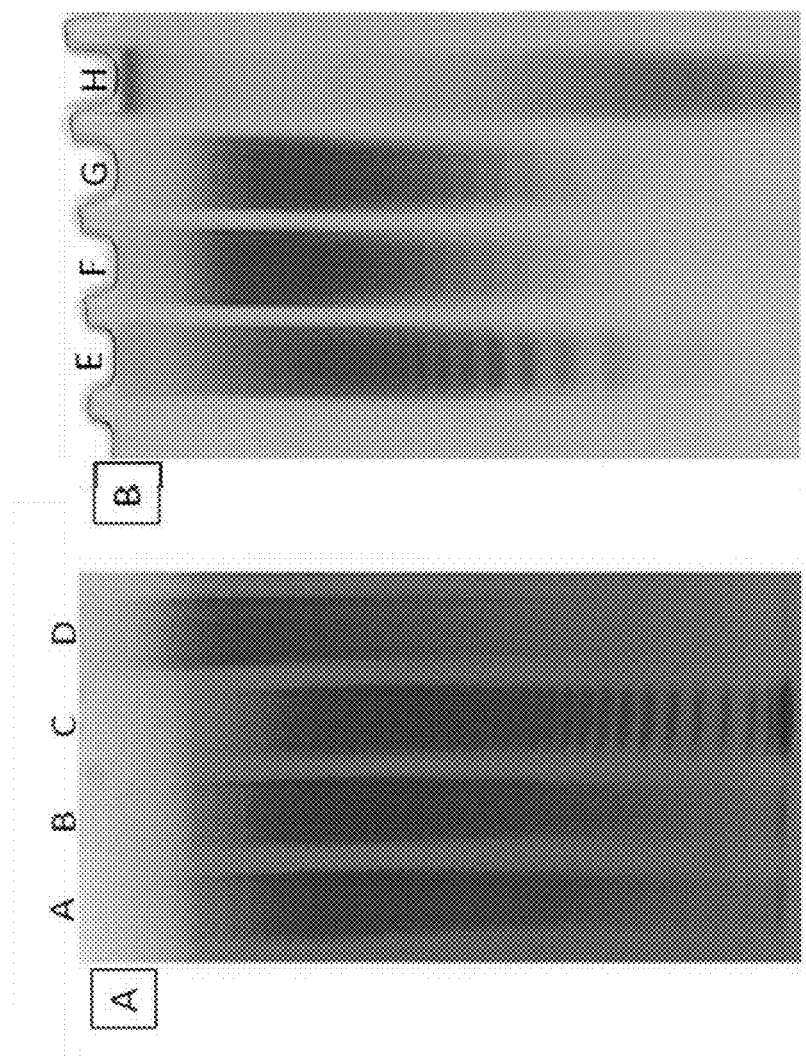
FIG. 3A shows native polyacrylamide gel electrophoresis (PAGE) analysis of (A) FOS HA (2) 10 kDa, (B) FOS HA (1) 10 kDa, (C) FOS BHA, and (D) POS BHA. A 10 µg aliquot of each sample was separated on a Novex® Tris-Glycine 18% gel (Invitrogen, Carlsbad, Calif.) run at 125 V for 1.5 hours under native conditions.
FIG. 3B shows native PAGE analysis of (E) FOS HA manufactured from Kewpie's Hyalo Oligo HA using pyridine-sulfur trioxide complex, (F) FOS HA manufactured from Novozymes HA using pyridine-sulfur trioxide complex, (G) POS HA manufactured from Novozymes HA using pyridine-sulfur trioxide complex, and (H) FOS HA 10 kDa manufactured from sulfur trioxide N,N-dimethylformamide complex. An aliquot (15 µg) of each sample was separated on a 20% acrylamide IDSmart Gel (Boca Scientific, Boca Raton, Fla.) run at 125 V for 75 minutes under native conditions. Gels were stained in an aqueous solution of 0.08% azure A.

FIG. 3a shows native polyacrylamide gel electrophoresis (PAGE) analysis of (A) FOS HA (2) 10 kDa, (B) FOS HA (1) 10 kDa, (C) FOS BHA, and (D) POS BHA. 10 μg of each sample was separated on a Novex® Tris-Glycine 18% gel (Invitrogen, Carlsbad, Calif.) run at 125 V for 1.5 hours under native conditions. FIG. 3b shows native PAGE analysis of (E) FOS HA manufactured from Kewpie's Hyalo Oligo HA using pyridine-sulfur trioxide complex, (F) FOS HA manufactured from Novozymes HA using pyridine-sulfur trioxide complex, (G) POS HA manufactured from Novozymes HA using pyridine-sulfur trioxide complex, and (H) FOS HA 10 kDa manufactured from sulfur trioxide N,N-dimethylformamide complex. 15 μg of each sample was separated on a 20% acrylamide IDSmart Gel (Boca Scientific, Boca Raton, Fla.) run at 125 V for 75 minutes under native conditions. Gels were stained in an aqueous solution of 0.08% azure A.

III. In Vitro Studies a. Human Leukocyte Elastase (HLE) Inhibition Assay

To investigate the inhibitory effects of sulfated HA on leukocyte elastase, 100 μl of 7.5 μg/ml HLE was incubated with 100 μl of sulfated HA's at a range of concentrations from 0.001 to 100 μg/mL. The mixture was incubated for 10 minutes at 25° C., after which 50 μl of the HLE substrate suc-Ala-Ala-Val-pNA (1.5 mM) was added. Active HLE cleaves the substrate and produces chromogenic pNA which is followed by measuring the change in absorbance at 405 nm using a kinetic read. $IC_{50}$ values are obtained (Table 1) using a 4-parameter logistic non-linear regression equation of the Vmax (rate of absorption) versus sulfated HA concentration.

TABLE 1

Inhibition of Human Leukocyte Elastase (HLE)

| Sample | $IC_{50}$ value (μg/ml) |
|---|---|
| POS BHA | 0.30 |
| FOS BHA | 0.18 |
| F-OSHA(2) 10k | 0.23 |
| F-OSHA(1) 10k | 0.22 |
| FOSHA Kewpie | 0.46 |
| FOSHA Novozymes | 0.45 |
| POSHA Novozymes | 0.47 |
| FOSHA Novozymes DMF | 0.76 | b. CML-BSA/RAGE Complex Inhibition Assay

The CML-BSA and RAGE complex inhibition assay was prepared by coating a polyvinyl chloride plate with 100 μl of 5 μg/ml CML-BSA. Separately, a 1 μg/ml solution of RAGE-Fc chimera in PBST-0.1% BSA was incubated with an equal volume of serially diluted sulfated low molecular weight hyaluronan and HA oligosaccharides at concentration ranges of 0.0005 μg/ml to 100 μg/ml overnight at 4° C. The following day, 50 μl of RAGE-sulfated HA mix was transferred to each respective ligand-coated well and incubated at 37° C. for 1 hour. Wells were then washed four times with PBST. To detect bound RAGE, 50 μl of 0.5 μg/ml of anti-RAGE antibody was added to each well. The plate was incubated for 1 hour at room temperature and the wells washed again four times with PBST. HRP-conjugated secondary antibody (50 μl per well) was added, wells were incubated for 1 hour at room temperature and then washed four times with PB ST. A colorimetric reaction was initiated by addition of 100 μl of TMB and terminated with the addition of 50 μl of 1 N HCl. Absorbance at 450 nm was plotted against the sulfated HA concentration and $IC_{50}$ values obtained (Table 2) using a 4-parameter logistic non-linear regression equation.

TABLE 2

Inhibition of CML-BSA binding to RAGE

| Sample | $IC_{50}$ value (μg/ml) |
|---|---|
| POS BHA | >100 |
| FOS BHA | 0.0468 |
| F-OSHA(2) 10k | 0.0176 |
| F-OSHA(1) 10k | 0.0197 |
| FOSHA Kewpie | 0.037 |

TABLE 2-continued

Inhibition of CML-BSA binding to RAGE

| Sample | $IC_{50}$ value (μg/ml) |
|---|---|
| FOSHA Novozymes | 0.023 |
| POSHA Novozymes | 0.066 |
| FOSHA Novozymes DMF | 0.521 | c. Characterization of the Pyridinium Adduct

Figure 5:
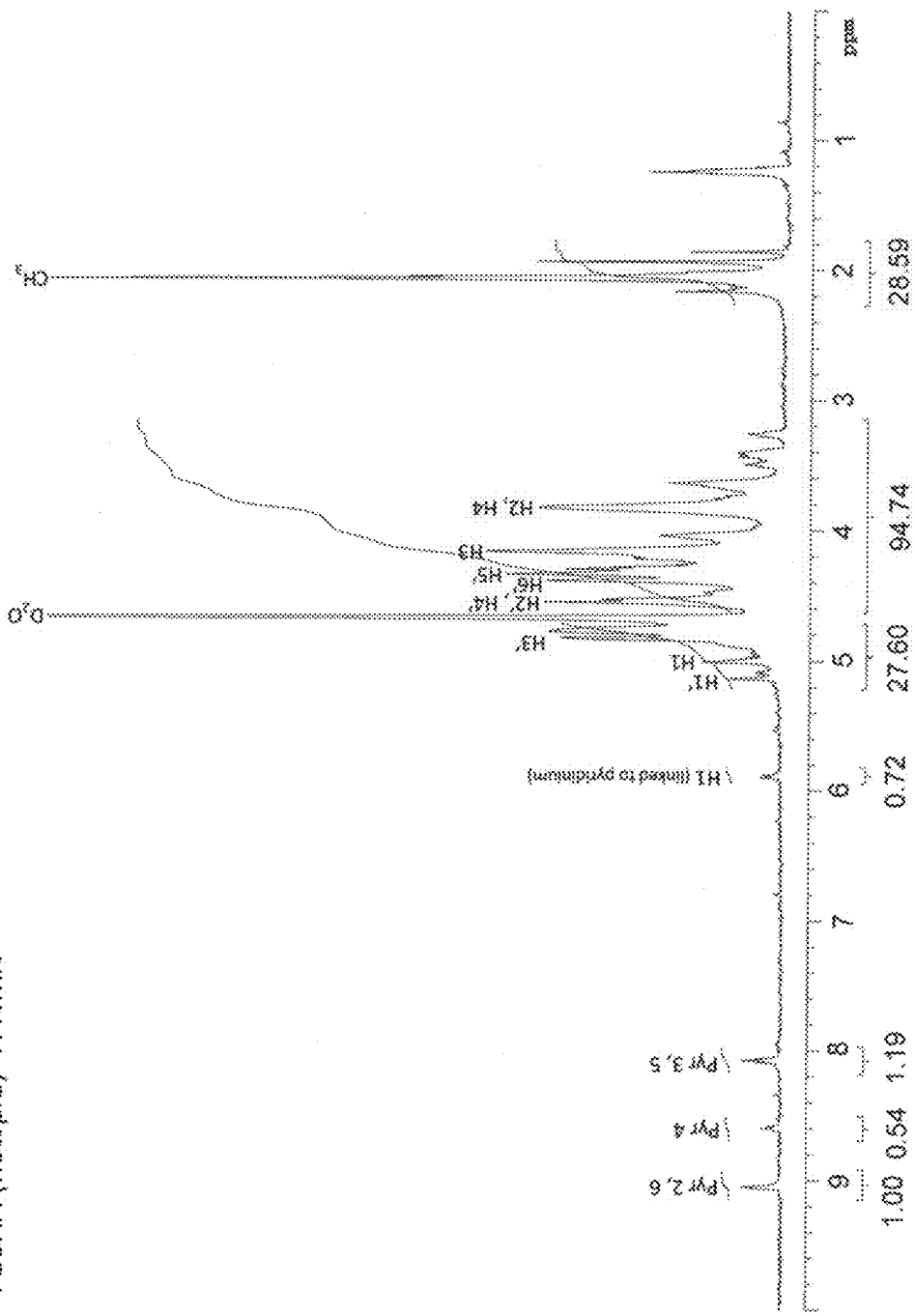
FIG. 5 is the $^1$H NMR spectrum of FOSHA-Kewpie-Pyr.SO$_3$, which reveals three peaks between 8.00 ppm and 9.10 ppm representing the pyridinium protons of the pyridinium adduct.

The pyridinium content of the sulfated HA samples prepared using the pyridine-sulfur trioxide complex was analyzed via UV absorbance. A standard curve was created using 1-butylpyridinium bromide (Sigma, St. Louis, Mo.) and the sulfated HA samples were diluted from 2 to 0.025 mg/ml as necessary for the UV measurements to fall within the standard curve. Absorbance values at 255 nm in a quartz cuvette were recorded for the standards and samples. From the standard curve, weight percent pyridinium values were calculated for each sample and are included in Table 3. The pyridinium adduct of FOSHA-Kewpie-Pyr.SO$_3$ was also characterized by $^{13}$C NMR spectroscopy and compared to published data. (Hintze V, Moeller S, Schnabelrauch M, Beirbaum S, Viola M, Worch H, Scharnweber D. "Modifications of Hyaluronan Influence the Interaction with Human Bone Morphogenetic Protein-4 (hBMP-4)" *Biomacromolecules* 10:3290-3297, 2009) The $^{13}$C NMR data is presented in Table 4. Finally, FIG. 5 is the $^1$H NMR spectrum of FOSHA-Kewpie-Pyr.SO$_3$, which reveals three peaks between 8.00 ppm and 9.10 ppm representing the pyridinium protons of the pyridinium adduct.

TABLE 3

Measurement of Pyridinium Content of Sulfated HA Created with Pyridine-Sulfur Trioxide Complex

| Sample | Average wt % pyridinium | Standard deviation |
|---|---|---|
| FOSHA Kewpie | 0.80 | 0.02 |
| FOSHA Novozymes | 0.462 | 0.009 |
| POSHA Novozymes | 0.662 | 0.006 |
| POS BHA | 0.11 | 0.03 |
| FOS BHA | 1.7 | 0.1 |
| F-OSHA(2) 10k | 14.7 | 0.8 |
| F-OSHA(1) 10k | 9.0 | 0.6 |

TABLE 4

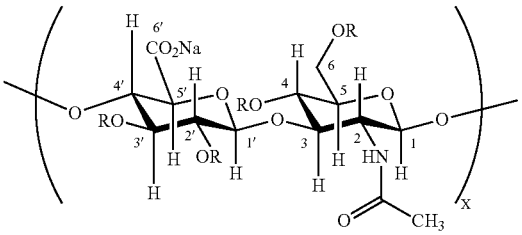

$^{13}$C NMR Data of FOSHA-Kewpie-Pyr.SO$_3$ compared with published data.

|  | Hya | sHya 1.0 (6.6% S) | sHya 2.8 (13.1% S) | FOSHA-Kewpie |
|---|---|---|---|---|
| C=O | 175.4 | 175.2 | 175.3 | 174.9 |
| C'=O (6') | 174.4 | 174.2 | 175.0 | 173.9 |
| C1' | 103.6 | 103.5 | 102.0 | 101.4 |
| C1 | 101.0 | 101.3 | 100.6 | 100.4 |
| C3 | 83.5 | 82.5 | 79.3-76.9 | 79.1-75.6 |

TABLE 4-continued

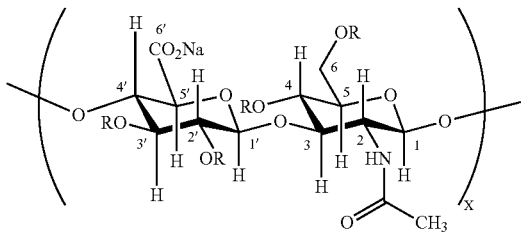

$^{13}$C NMR Data of FOSHA-Kewpie-Pyr.SO$_3$ compared with published data.

|  | Hya | sHya 1.0 (6.6% S) | sHya 2.8 (13.1% S) | FOSHA-Kewpie |
|---|---|---|---|---|
| C4' | 80.7 | 81.4 |  |  |
| C5' | 77.1 | 76.8 |  |  |
| C5 | 76.2 | 74.2 |  |  |
| C3' | 74.4 | 73.8 |  |  |
| C2' | 73.3 | 72.9 | 73.7 | 73.0 |
| C4 | 69.4 | 68.8 | 69.5$_{(small)}$ | 68.6 |
| C6 | 61.5 | 67.5 | 68.3 | 67.7 |
| C2 | 54.9 | 54.7 | 56.0 | 55.2 |
| CH$_3$ | 23.2 | 22.9 | 23.6 | 23.2 |
| Py 2,6 |  |  |  | 142.7 |
| Py 4 |  |  |  | 128.2 |
| Py 3,5 |  |  |  | 103.4 |

IV. In Vivo Studies a. Mouse Bladder Inflammation Model

Mouse bladders are sensitive to various inflammatory substances including LL-37 (cathelicidin peptide) and have served as an excellent animal model to study the potential therapeutic agents in inflammatory diseases including cystitis. In order to investigate the anti-inflammatory effects of sulfated HA, the protective effects of FOSHA derivatives were measured in a murine cystitis model. First, C57/BL6 adult female mice were anesthetized and a catheter was inserted into the bladder through the urethra. The bladders were washed by infusing and draining 0.9% sterile saline. Bladders were then pre-instilled with either 150 µL of saline, 10 mg/ml FOSHA (Kewpie) or 10 mg/ml FOSHA (Novozymes) for 1 hour. The bladders were emptied and then instilled with 150 µL of 320 µM LL-37 for an additional 1 hour. All animals were fully recovered without complications. Twenty-four hours after the completion of the procedure, the bladders were removed, photographed, and frozen for MPO analysis.

b. Myeloperoxidase (MPO) Assay

Figure 2:
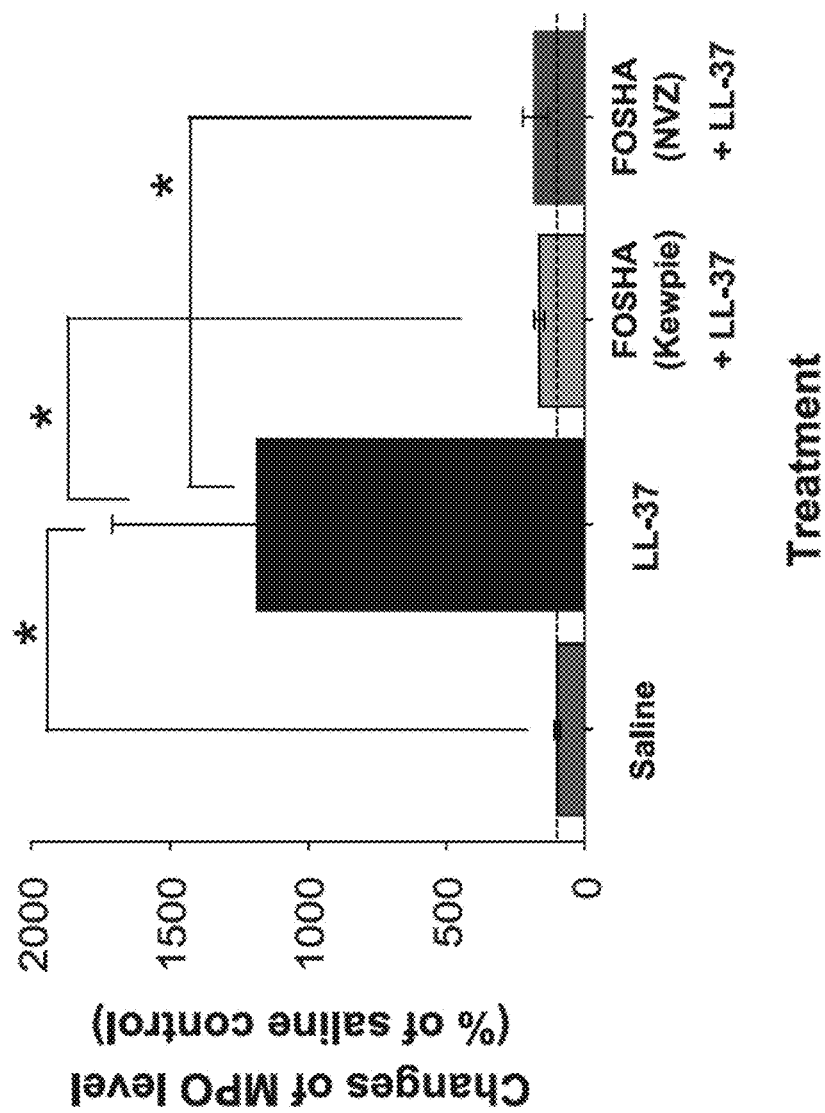
FIG. 2 shows the protective effect of fully-sulfated hyaluronan in the mouse model of LL-37 induced cystitis. Mouse bladders pre-instilled with either FOSHA (Kewpie) or FOSHA (NVZ) show significantly reduced MPO levels. The dashed line corresponds to the MPO level in control bladders treated with saline and without inflammation (100%). Values are the mean percent levels of MPO compared to the saline control. *$p<0.05$ (n=3 or 4). Error bars indicate standard error of mean.

The major cellular responses to inflammatory substances are secretion of various cytokines from damaged cells that recruit various immune cells to the target site. MPO is a peroxidase enzyme expressed abundantly in polymorphonuclear cells, which are primary cells recruited to the site of inflammation during the early stage of inflammation and therefore, MPO is an excellent marker to quantitatively measure the degree of inflammation. To analyze the anti-inflammatory effects of fully-sulfated HA in the murine cystitis model, the quantity of expressed MPO was measured in the bladders pre-treated with sulfated HA and compared with the levels of expressed MPO in untreated bladders and a saline control. Bladders were weighed and homogenized. The homogenized samples were centrifuged at 5,000 rpm to separate the soluble fraction from tissue debris and the concentration of MPO in the tissue homogenates (ng/mg tissue) was measured using the mouse MPO ELISA kit (HK210, Hycult biotech, The Netherlands) and expressed as percent difference from the saline instilled control (normal bladder without inflammation). Results are provided in FIG. 2.

To determine whether pretreatments of sulfated HA reduce tissue MPO concentration induced by instilled LL-37, we performed statistical analysis using one-way ANOVA followed by Tukey-Kramer multiple comparisons test using GraphPad InStat software (Version 3.1, GraphPad Software, Inc.). Statistical significance was set at p<0.0.

c. Conclusions

The results from the in vitro studies demonstrate the importance of the degree of sulfation with respect to RAGE antagonist activities (Table 2). Partial sulfation (less than 6% sulfur) results in a much less potent RAGE antagonist. Sulfated HA compounds with a MW less than 2,000 Da also show reduced potency in the in vitro assays. Fully-sulfated HA compounds, including those possessing the pyridinium adduct in excess of 1% w/w, showed good in vivo efficacy in reducing inflammation in the mouse model of bladder inflammation.

Throughout this application, various publications are referenced. The disclosures of these publications in their entireties are hereby incorporated by reference into this application in order to more fully describe the compounds, compositions and methods described herein.

Various modifications and variations can be made to the compounds, compositions and methods described herein. Other aspects of the compounds, compositions and methods described herein will be apparent from consideration of the specification and practice of the compounds, compositions and methods disclosed herein. It is intended that the specification and examples be considered as exemplary.

What is claimed:

1. A method for reducing or preventing inflammation in a subject comprising administering to the subject sulfated hyaluronan or a pharmaceutically acceptable salt or ester thereof, or a combination thereof, wherein (1) 100% of the primary C-6 hydroxyl protons of the N-acetyl-glucosamine residues of the sulfated hyaluronan are substituted with a sulfate group, (2) the sulfated hyaluronan has a degree of sulfation from greater than 3.5 to less than or equal to 4.0, (3) the sulfated hyaluronan has an average molecular weight from 1 kDa to 3 kDa, and (4) pyridine covalently attached to the sulfated hyaluronan.

2. The method of claim 1, wherein the pharmaceutically acceptable ester is a prodrug.

3. The method of claim 1, wherein the sulfated hyaluronan or the pharmaceutically acceptable salt or ester thereof is administered as a pharmaceutical composition.

4. The method of claim 3, wherein the composition comprises a capsule, a tablet, a chewing gum, a lozenge, a powder, an ointment, a lotion, a cream, a paste, a mouthwash, a spray, a suppository, an enema, an aerosol, or a beverage.

5. The method of claim 3, wherein the composition is administered ophthalmically, vaginally, rectally, intranasally, or applied directly to the oral mucosa, gingival, or periodontal pocket.

6. The method of claim 3, wherein the composition further comprises an anti-inflammatory agent, an anti-pyretic agent, steroidal and non-steroidal drugs for anti-inflammatory use, a hormone, a growth factor, a contraceptive agent, an antiviral, an antibacterial, an antifungal, an analgesics, a hypnotic, a sedative, a tranquilizer, an anti-convulsant, a muscle relaxant, a local anesthetic, an antispasmodic, an antiulcer drug, a peptidic agonist, a sympathomimetic agent, a cardiovascular agent, an antitumor agent, or an oligonucleotide.

7. The method of claim 1, wherein the pharmaceutically acceptable salt comprises an organic salt, a metal salt, or a combination thereof.

8. The method of claim 1, wherein the pharmaceutically acceptable salt comprises a salt selected from the group consisting of $NH_4^+$, $Na^+$, $Li^+$, $K^+$, $Ca^{+2}$, $Mg^{+2}$, $Fe^{+2}$, $Fe^{+3}$, $Cu^{+2}$, $Al^{+3}$, $Zn^{+2}$, 2-trimethylethanolammonium cation (choline), or a quaternary salt of isopropylamine, trimethylamine, diethylamine, triethylamine, tripropylamine, ethanolamine, 2-dimethylaminoethanol, 2-diethylaminoethanol, lysine, arginine, and histidine.

9. The method of claim 1, wherein the inflammation is produced by cancer, multiple sclerosis, osteoarthritis, rheumatoid arthritis, Alzheimer's beta amyloid peptide, periodontal disease, gingivitis, peri-implantitis, diabetic nephropathy, inflammatory bowel disease, asthma, rhinitis, rhinosinusitis, chronic obstructive pulmonary disease, acute lung injury, cystic fibrosis, sickle cell anemia, a cardiovascular inflammatory disorder, a pulmonary inflammatory disorder, an ocular inflammatory disorder, a cerebral inflammatory disorder or an intestinal inflammatory disorder.

10. The method of claim 1, wherein the inflammation is caused by a respiratory disorder.

11. The method of claim 10, wherein the respiratory disorder is cystic fibrosis, bronchiectasis, rhinitis, sinusitis, emphysema and chronic bronchitis (COPD), acute lung injury/adult respiratory distress syndrome, interstitial lung fibrosis, SARS, asthma, and respiratory syncytial virus.

12. The method of claim 10, wherein the inflammation is caused by a respiratory pathogen comprising *Streptococcus pneumoniae, Hemophilus influenzae, Staphylococcus, Mycoplasma pneumoniae*, Chlamydial pneumonia, or Gram negative bacteria.

13. The method of claim 1, wherein the inflammation is caused by otitis media.

14. The method of claim 1, wherein the inflammation is caused by a gastrointestinal disease or a bowel disease.

15. The method of claim 14, wherein the gastrointestinal disease is ulcerative colitis, Crohn's disease of the bowel, or hemorrhoids.

16. The method of claim 1, wherein the inflammation is caused by radiation-induced dermatitis.

17. The method of claim 1, wherein the inflammation is caused by a periodontal disease.

18. The method of claim 1, wherein the inflammation is caused by an ophthalmic disorder.

19. The method of claim 18, wherein the ophthalmic disorder is age-related macular degeneration, diabetic retinopathy, dry eye syndrome, conjunctivitis, iritis, uveitis, allergic conjunctivitis, inflammation caused by cataract surgery, or corneal inflammation.

20. The method of claim 1, wherein the sulfated hyaluronan or the pharmaceutically acceptable salt or ester thereof prevents ocular inflammation or scarring.

21. The method of claim 3, wherein the composition comprises eye drops that are applied directly to the surface of the eye.

22. The method of claim 3, wherein the composition is administered intraocularly.

23. The method of claim 1, wherein the inflammation is caused by surgery.

24. The method of claim 1, wherein the sulfated hyaluronan or the pharmaceutically acceptable salt or ester thereof, or a combination thereof treats inflammation.

25. The method of claim 1, wherein the sulfated hyaluronan or the pharmaceutically acceptable salt or ester thereof, or a combination thereof prevents inflammation.

* * * * *